(12) United States Patent
Agrawal

(10) Patent No.: US 6,815,429 B2
(45) Date of Patent: Nov. 9, 2004

(54) MODULATION OF OLIGONUCLEOTIDE CPG-MEDIATED IMMUNE STIMULATION BY POSITIONAL MODIFICATION OF NUCLEOSIDES

(75) Inventor: Sudhir Agrawal, Shrewsbury, MA (US)

(73) Assignee: Hybridon, Inc., Cambridge, MA (US)

( * ) Notice: Subject to any disclaimer, the term of this patent is extended or adjusted under 35 U.S.C. 154(b) by 196 days.

(21) Appl. No.: 09/770,602

(22) Filed: Jan. 26, 2001

(65) Prior Publication Data

US 2002/0055475 A1 May 9, 2002

Related U.S. Application Data

(60) Provisional application No. 60/178,562, filed on Jan. 26, 2000.

(51) Int. Cl.$^7$ .......................... A01N 43/04; C12Q 1/68; C12P 19/34; C12N 15/63; C07H 21/02
(52) U.S. Cl. ............................ 514/44; 435/6; 435/91.1; 435/375; 435/455; 536/23.1
(58) Field of Search ........................ 435/6, 91.1, 91.31, 435/91.5, 440, 375, 455; 514/44; 536/23.1, 24.5

(56) References Cited

U.S. PATENT DOCUMENTS

| 5,149,798 A | | 9/1992 | Agrawal et al. ............... 536/27 |
| 5,801,154 A | * | 9/1998 | Baracchini et al. ............ 514/44 |
| 5,886,165 A | | 3/1999 | Kandimalla et al. ........ 536/23.1 |

FOREIGN PATENT DOCUMENTS

| WO | WO 98/00564 | 1/1998 | ............ C12Q/1/68 |
| WO | WO 98/49288 | 11/1998 | ........... C12N/15/11 |

OTHER PUBLICATIONS

Agrawal et al, Molecular Med. Today, 2000, vol. 6, pp 72–81.*
McCluskie et al. Mole. Med. 1999, vol. 1, pp 287–300.*
Weiner, G. J. of Leukocyte Biol. 2000, vol. 68, pp. 455–462.*
Krieg et al. Immunology Today. 2000. vol. 221, No. 10, pp. 521–526.*
Khorana et al. (1972) "Studies on Polynucleotides," *J. Molec. Biol.* 72:209.
Reese (1978) "The Chemical Synthesis of Oligo– and Poly– Nucleotides By The Phosporotriester Appraoch," *Tetrahedron* 34:3143–3179.
Beaucage et al. (1981) "Deoxynucleoside Phosphoramidites—A New Class of Key Intermediates for Deoxypolynucleotide Synthesis," *Tetrahedron Lett.* 22:1859–1862.
Connolly et al. (1984) "Synthesis and Characterization of an Octanucleotide Containing the EcoRI Recognition Sequence With A Phosphorothioate Group At The Cleavage Site," *Biochemistry* 23:3443.
Agrawal et al. (1987) "Oligodeoxynucleotise Methylphosphonates: Synthesis and Enzymic Degradation," *Tetrahedron Lett.* 28(31):3539–3542.
Jager et al. (1988) Oligonucleotide N–Alkylphosphoroamidates: Synthesis and Binding to Polynucleotides, *Biochemistry* 27:7237.
Agrawal et al. (1988) Oligodeoxynucleoside Phosphoroamidates and Phosporothioates As Inhibitors of Human Immunodeficiency Virus, *Proc. Natl. Acad. Sci. USA* 85:7079–7083.
Zon et al. (1991) "Phosphorothioate Oligonculeotides" *Oligonucleotides and Analogues: A Practical Approach* pp. 87–108.
Kuramoto et al. (1992) "Oligonucleotide Sequences Required For Natural Killer Cell Activation," *Jpn. J. Cancer Res.* 83:1128–1131.
Crooke (ed) (1993) *Antisense Research and Applications* CRC Press, Boca Raton, Florida.
McIntyre et al. (1993) "A Sense Phosphorothioate Oligonucleotide Directed to the Initiation Codon of Transcription Factor NF–kB p65 Causes Sequence–Specific Immune Stimulation," *Antisense Res. Dev.* 3:309–322.
Zon (1993) "Protocols for Oliognucleotides and Analogs," *Methods in Molecular Biology* vol. 20, pp. 165–189.
Agrawal et al. (1995) "Modified Oligonucleotides as Therapeutic and Diagnositc Agents," *Curr.Opin.Biotechnol.* 6:12–19.
Crooke (1998) "An Overview of Progress in Antisense Therapeutics," *Antisense Nucleic Acid Drug Dev.* 8:115–122.
Krieg et al. (1995) "CpG Motifs in Bacterial DNA Trigger Direct B–Cell Activation," *Nature* 371:546–549.
Liang et al. (1996) "Activation of Human B Cells By Phosphorothioate Oligodeoxynucleotides," *J. Clin. Invest.* 98:1119–1129.
Zhao et al. (1996) "Effect of Different Chemically Modified Oligodeoxynucleotides on Immune Stimulation," *Biochem. Pharm.* 51:173–182.
Krieg (1998) "Leukocyte Stimulation by Oligodeoxynucleotides," *Appl. Antisense Oligo. Tech.* 24:431–447.
McCluskie et al. (1998) "Cutting Edge: CpG DNA Is A Potent Enhancer of Systemic and Mucosal Immune Responses Against Hepatitis B Surface Antigen with Intransal Administration to Mice," *J. Immunol.* 161:4463–4466.

(List continued on next page.)

Primary Examiner—John L. LeGuyader
Assistant Examiner—Jane Zara
(74) Attorney, Agent, or Firm—Keown & Associates

(57) ABSTRACT

The invention provides methods for modulating the immune response caused by CpG-containing oligonucleotides. The methods according to the invention enable both decreasing the immunostimulatory effect for antisense applications, as well as increasing the immunostimulatory effect for immunotherapy applications.

8 Claims, 2 Drawing Sheets

OTHER PUBLICATIONS

Moldoveanu et al. (1998) "CpG DNA, A Novel Immune Enhancer for Systemic and Mucosal Immunization With Influenza Virus," *Vaccine* 16:1216–1224.

Agrawal (1999) "Importance of Nucleotide Sequence and Chemical Modifications of Antisense Oligonucleotides," *Biochemica et Biophysica Acts* 1489:53–68.

Kumar et al. (1999) "Properties of Mixed Backbone Oligonucleotides Containing 3'-O-Methyl Ribonucleosides," *Bioorg. & Med. Chem.* 9:2515:2520.

Pisetsky et al. (1999) "Influence of Backbone Chemistry on Immune Activation by Synthetic Oligonucleotides," *Biochem. Phar.* 58:1981–1988.

Zhao et al. (1999) "Site of Chemical Modification in CpG Containing Phosphorothioate Oligodeoxynucleotide Modulates Its Immunostimulatory Activity," *Bioorg. & Med. Chem. Lett.* 9:3453–3458.

Zhao et al. (2000) "Immunostimulatory Activity of CpG Containing Phosphorothioate Oligodeoxynucleotide is Modulated by Modification of a Single Deoxynucleoside," *Bioorg. & Med. Chem. Lett.* 10:1051–1054.

* cited by examiner

SEQ. ID NO.

| | | |
|---|---|---|
| 1 | 113-1 | TCCATGACGTTCCTGATGC |
| 6 | 77-2 | TCCA_T_GACGTTCCTGATGC |
| 4 | 77-3 | TCC_A_TGACGTTCCTGATGC |
| 7 | 77-4 | TCCATGACG_T_TCCTGATGC |
| 8 | 77-5 | TCCATGACGT_T_CCTGATGC |

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tccatgacgt tcctgatgc                                                      19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 3'-O-methyl modification

<400> SEQUENCE: 2
tccatgacgt tcctgatgc                                                      19

<210> SEQ ID NO 3
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 3'-O-methyl modification

<400> SEQUENCE: 3
tccaugacgt tcctgatgc                                                      19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 3'-O-methyl modification

<400> SEQUENCE: 4
tccatgacgt tcctgatgc                                                      19

<210> SEQ ID NO 5
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic oligonucleotide

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 3'-O-methyl modification

<400> SEQUENCE: 5
tccatgacgu tcctgatgc                                               19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 3'-O-methyl modification

<400> SEQUENCE: 6
tccatgacgt tcctgatgc                                               19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 3'-O-methyl modification

<400> SEQUENCE: 7
tccatgacgt tcctgatgc                                               19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)
<223> OTHER INFORMATION: 3'-O-methyl modification

<400> SEQUENCE: 8
tccatgacgt tcctgatgc                                               19
```

US 6,815,429 B2

MODULATION OF OLIGONUCLEOTIDE CPG-MEDIATED IMMUNE STIMULATION BY POSITIONAL MODIFICATION OF NUCLEOSIDES

CROSS-REFERENCE TO RELATED APPLICATION

This application claims priority to U.S. provisional application Ser. No. 60/178,562, filed Jan. 26, 2000, the entire contents of which are hereby incorporated by reference.

BACKGROUND OF THE INVENTION

1. Field of the Invention

The invention relates to the therapeutic use of oligonucleotides, both in the antisense approach, and as immunostimulatory agents.

2. Summary of the Related Art

Oligonucleotides have become indispensible tools in modem molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology*, Vol 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, *Curr. Op. in Biotech*. 6: 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol*. 72: 209 (1972) discloses phosphodiester chemistry for oligonucleotide synthesis. Reese, *Tetrahedron Lett*. 34: 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett*. 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modem approaches have been used to synthesize oligonucleotides having a variety of modified internucleotide linkages. Agrawal and Goodchild, *Tetrahedron Lett*. 28: 3539–3542 (1987), teaches synthesis of oligonucleotide methylphosphonates using phosphoramidite chemistry. Connolly et al., *Biochemistry* 23:3443 (1984), discloses synthesis of oligonucleotide phosphorothioates using phosphoramidite chemistry. Jager et al., *Biochemistry* 27: 7237 (1988), discloses synthesis of oligonucleotide phosphoramidates using phosphoramidite chemistry. Agrawal et al., *Proc. Antl. Acad. Sci. USA* 85: 7079–7083 (1988), discloses synthesis of oligonucleotide phosphoramidates and phosphorothioates using H-phosphonate chemistry.

More recently, several researchers have demonstrated the validity of the antisense approach to therapeutic treatment of disease. Crooke, *Antisense Nucleic Acid Drug Dev*. 8: vii–viii, discloses the successful marketing approval of a phosphorothioate oligonucleotide for the treatment of human cytomegalovirus-induced retinitis. Unfortunately, the use of phosphorothioate oligonucleotides has become more complex than originally expected. Certain effects caused by phosphorothioate oligonucleotides could not be explained by the expected antisense mechanism. For example, McIntyre et al., *Antisense Res. Dev*. 3: 309–322 (1993) teaches that a "sense" phosphorothioate oligonucleotide causes specific immune stimulation. This and other side effects have complicated the picture for phosphorothioate oligonucleotides.

On the other hand, the observation that phosphodiester and phosphorothioate oligonucleotides can induce immune stimulation has created interest in developing this side effect as a therapeutic tool. These efforts have focussed on phosphorothioate oligonucleotides containing the dinucleotide CpG. Kuramoto et al., *Jpn. J. Cancer Res*. 83: 1128–1131 (1992) teaches that phosphodiester oligonucleotides containing a palindrome that includes a CpG dinucleotide can induce interferon-alpha and gamma synthesis and enhance natural killer activity. Krieg et al., *Nature* 371: 546–549 (1995) discloses that phosphorothioate CpG-containing oligonucleotides are immunostimulatory. Liang et al., *J. Clin. Invest*. 98: 1119–1129 (1996) discloses that such oligonucleotides activate human B cells. Moldoveanu et al., *Vaccine* 16: 1216–124 (1998) teaches that CpG-containing phosphorothioate oligonucleotides enhance immune response against influenza virus. McCluskie and Davis, *The Journal of Immunology* 161: 4463–4466 (1998) teaches that CpG-containing oligonucleotides act as potent adjuvants, enhancing immune response against hepatitis B surface antigen.

These reports make clear that there is a need to be able to modulate the immune response caused by CpG-containing oligonucleotides. Ideally, such modulation should include decreasing the immunostimulatory effect for antisense applications, as well as increasing the immunostimulatory effect for immunotherapy applications.

BRIEF SUMMARY OF THE INVENTION

The invention provides methods for modulating the immune response caused by CpG-containing oligonucleotides. The methods according to the invention enables both decreasing the immunostimulatory effect for antisense applications, as well as increasing the immunostimulatory effect for immunotherapy applications. Thus, the invention further provides oligonucleotides having optimal levels of immunostimulatory effect for either application and methods for making and using such oligonucleotides.

The present inventor has surprisingly discovered that positional modification of CpG-containing oligonucleotides dramatically affects their immunostimulatory capabilities. In particular, 3' alkylation or alkoxylation of oligonucleotides, or introduction of an uncharged internucleoside linkage, at particular positions 5' or 3' to the CpG dinucleotide either enhances or reduces their immunostimulatory effect in a reproducible and predictable manner.

In a first aspect, the invention provides a method for reducing the immunostimulatory effect of a CpG-containing oligonucleotide. The method according to this aspect of the invention comprises introducing a 3' substituted nucleoside into the oligognucleotide at a position adjacent to, and on the 5' and/or 3' side of the CpG dinucleotide. In preferred embodiments, this method includes creating a 2'–5' linkage between the 2' position of a 3' substituted nucleoside and the 5' position of another nucleoside, which may or may not be a 3' substituted nucleoside.

In a second aspect, the invention provides a CpG-containing oligonucleotide having a reduced immunostimulatory effect, wherein the oligonucleotide comprises a 3' substituted nucleoside at a position adjacent to, and on the 5' and/or 3' side of the CpG dinucleotide. In preferred embodiments, CpG-containing oligonucleotides according to this aspect of the invention include a 2'–5' linkage between the 2' position of a 3' substituted nucleoside and the 5' position of another nucleoside, which may or may not be a 3' substituted nucleoside.

In a third aspect, the invention provides a method for obtaining an antisense-specific reduction in the expression of a gene in a mammal, the method comprising administering to the mammal a CpG-containing oligonucleotide having a reduced immunostimulatory effect, wherein the oligonucleotide comprises a 3' substituted nucleoside at a position adjacent to, and on the 5' and/or 3' side of the CpG dinucleotide. In preferred embodiments, CpG-containing oligonucleotides used in this aspect of the invention include a 2'–5' linkage between the 2' position of a 3' substituted nucleoside and the 5' position of another nucleoside, which may or may not be a 3' substituted nucleoside.

In a fourth aspect, the invention provides a method for reducing the immunostimulatory effect of a CpG-containing oligonucleotide. The method according to this aspect of the invention comprises introducing an uncharged internucleoside linkage into the oligonucleotide at a position adjacent to, and on the 5' side of the CpG dinucleotide.

In an fifth aspect, the invention provides a CpG-containing oligonucleotide having a reduced immunostimulatory effect, wherein the oligonucleotide comprises an uncharged internucleoside linkage at a position adjacent to, and on the 5' side of the CpG dinucleotide.

In a sixth aspect, the invention provides a method for obtaining an antisense-specific reduction in the expression of a gene in a mammal, the method comprising administering to the mammal a CpG-containing oligonucleotide having a reduced immunostimulatory effect, wherein the oligonucleotide comprises an uncharged internucleoside linkage at a position adjacent to, and on the 5' side of the CpG dinucleotide.

In a seventh aspect, the invention provides a method for reducing the immunostimulatory effect of a CpG-containing oligonucleotide. The method according to this aspect of the invention comprises introducing a 2'–5' internucleoside linkage into the oligonucleotide at a position adjacent to, and on the 5' side of the CpG dinucleotide.

In an eighth aspect, the invention provides a CpG-containing oligonucleotide having a reduced immunostimulatory effect, wherein the oligonucleotide comprises a 2'–5' internucleoside linkage at a position adjacent to, and on the 5' side of the CpG dinucleotide.

In a ninth aspect, the invention provides a method for obtaining an antisense-specific reduction in the expression of a gene in a mammal, the method comprising administering to the mammal a CpG-containing oligonucleotide having a reduced immunostimulatory effect, wherein the oligonucleotide comprises a 2'–5' internucleoside linkage at a position adjacent to, and on the 5' side of the CpG dinucleotide.

In a tenth aspect, the invention provides a method for increasing the immunostimulatory effect of a CpG-containing oligonucleotide. The method according to this aspect of the invention comprises introducing into the oligonucleotide a 3' substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide. In preferred embodiments, this method includes creating a 2'–5' linkage between the 2' position of a 3' substituted nucleoside and the 5' position of another nucleoside, which may or may not be a 3' substituted nucleoside.

In a eleventh aspect, the invention provides CpG-containing oligonucleotides having increased immunostimulatory effects, the oligonucleotide comprising a 3' substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain embodiments, the oligonucleotide is not an antisense oligonucleotide. In preferred embodiments, CpG-containing oligonucleotides according to this aspect of the invention include a 2'–5' linkage between the 2' position of a 3' substituted nucleoside and the 5' position of another nucleoside, which may or may not be a 3' substituted nucleoside.

In an twelfth aspect, the invention provides a method for inducing an immune response in a mammal, the method comprising administering to the mammal an oligonucleotide comprising a 3'-substituted nucleoside at a position selected from the group consisting of 3rd nucleoside 5' to the CPG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide. In preferred embodiments, CpG-containing oligonucleotides used in this aspect of the invention include a 2'–5' linkage between the 2' position of a 3' substituted nucleoside and the 5' position of another nucleoside, which may or may not be a 3' substituted nucleoside.

In a thirteenth aspect, the invention provides a method for increasing the immunostimulatory effect of a CpG-containing oligonucleotide. The method according to this aspect of the invention comprises introducing into the oligonucleotide an uncharged internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide.

In a fourteenth aspect, the invention provides CpG-containing oligonucleotides having increased immunostimulatory effects, the oligonucleotide comprising an uncharged internucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof.

In a fifteenth aspect, the invention provides a method for inducing an immune response in a mammal, the method comprising administering to the mammal an oligonucleotide comprising an uncharged internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide.

In a sixteenth aspect, the invention provides a method for increasing the immunostimulatory effect of a CpG-containing oligonucleotide. The method according to this aspect of the invention comprises introducing into the oligonucleotide a 2'–5' internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide.

In a seventeenth aspect, the invention provides CpG-containing oligonucleotides having increased immunostimulatory effects, the oligonucleotide comprising a 2'–5' internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof.

In an eighteenth aspect, the invention provides a method for inducing an immune response in a mammal, the method comprising administering to the mammal an oligonucleotide comprising a 2'–5' internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide.

DETAILED DESCRIPTION OF THE PREFERRED EMBODIMENTS

Figure 1:
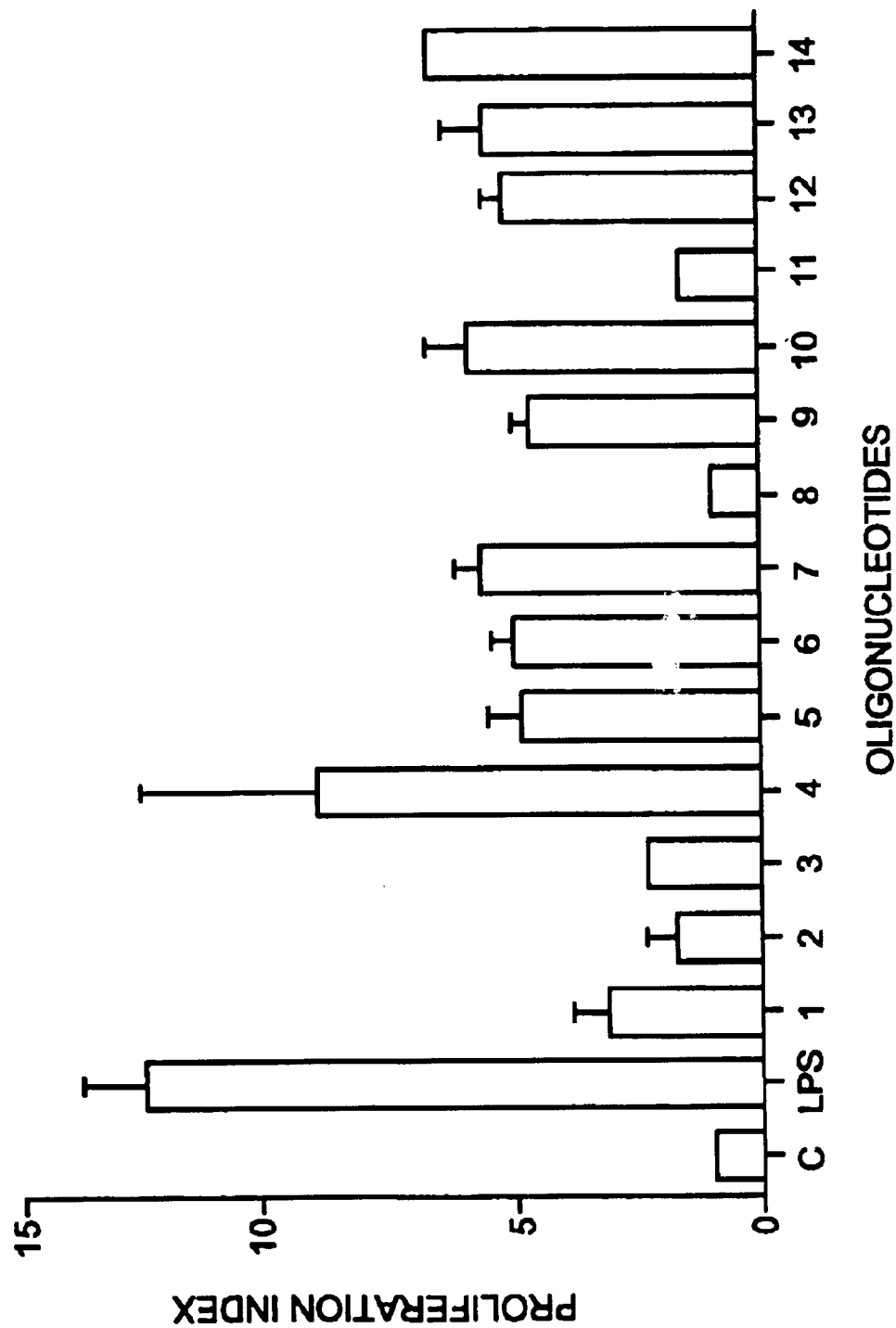
FIG. 1 shows results of a proliferation assay of mouse spleen cells in the presence of no oligonucleotide (C), lipopolysaccharide (LPS), or various unsubstituted or 2' or 3' substituted oligonucleotides.

The invention relates to the therapeutic use of oligonucleotides, both in the antisense approach, and as immunostimulatory agents. The patents and publications cited herein reflect the level of knowledge in the field and are hereby incorporated by reference in their entirety. In the event of conflict between any teaching of any reference cited herein and the present specification, the latter shall prevail, for purposes of the invention.

The invention provides methods for modulating the immune response caused by CpG-containing oligonucleotides. The methods according to the invention enables both decreasing the inmmunostimulatory effect for antisense applications, as well as increasing the immunostimulatory effect for immunotherapy applications. Thus, the invention further provides oligonucleotides having optimal levels of immunostimulatory effect for either application and methods for making and using such oligonucleotides.

The present inventor has surprisingly discovered that positional modification of CpG-containing oligonucleotides dramatically affects their immunostimulatory capabilities. In particular, 3' alkylation or alkoxylation of oligonucleotides, or introduction of an uncharged internucleoside linkage, at particular positions 5' or 3' to the CpG dinucleotide either enhances or reduces their immunostimulatory effect in a reproducible and predictable manner.

As used for the first nine aspects of the invention, the term "complementary" means having the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such hybridization can be inferred from the observation of specific gene expression inhibition.

As used for the first nine aspects of this invention, "antisense activity" means that the oligonucleotide, when introduced into a cell or an animal, causes a reduction in the expression of the gene to which it is complementary.

In a first aspect, the invention provides a method for reducing the immunostimulatory effect of a CpG-containing oligonucleotide. The method according to this aspect of the invention comprises introducing a 3' substituted nucleotide into the oligonucleotide at a position adjacent to, and on the 5' and/or 3' side of the CpG dinucleotide. In preferred embodiments, this method includes creating a 2'–5' linkage between the 2' position of a 3' substituted nucleoside and the 5' position of another nucleoside, which may or may not be a 3' substituted nucleoside.

The method according to this aspect of the invention can be conveniently carried out using any of the well-known synthesis techniques by simply using the appropriate 3' substituted monomer synthon in the synthesis process in the cycle immediately following the incorporation of the CpG dinucleotide. Preferred monomers include phosphoramidites, phosphotriesters and H-phosphonates. Thus, for purposes of the invention, "introducing a 3' substituted nucleotide into the oligonucleotide at a position adjacent to, and on the 5' side of the CpG dinucleotide" simply means synthesizing an oligonucleotide that has a 3' substituted nucleoside at such a position. Synthesis of oligonucleotides containing 3' substituted nucleosides has recently been described by Kumar and Takaku, Bioorganic & Medicinal Chemistry Letters 9: 2515–2520 (1999).

In a second aspect, the invention provides a CpG-containing oligonucleotide having a reduced immunostimulatory effect, wherein the oligonucleotide comprises a 3' substituted nucleoside at a position adjacent to, and on the 5' and/or 3' side of the CpG dinucleotide. In preferred embodiments, CpG-containing oligonucleotides according to this aspect of the invention include a 2'–5' linkage between the 2' position of a 3' substituted nucleoside and the 5' position of another nucleoside, which may or may not be a 3' substituted nucleoside.

Preferably, such oligonucleotides will have from about 12 to about 50 nucleotides, most preferably from about 12 to about 35 nucleotides. Preferred oligonucleotides according to this aspect of the invention are complementary to a gene or gene transcript. More preferably, such oligonucleotides have antisense activity. In some preferred embodiments, the oligonucleotide has only one 3' substituted nucleoside for each CpG dinucleotide present in the oligonucleotide. In some preferred embodiments, the oligonucleotide has only one 3' substituted nucleoside.

In a third aspect, the invention provides a method for obtaining an antisense-specific reduction in the expression of a gene in a mammal, the method comprising administering to the mammal a CpG-containing oligonucleotide having a reduced immunostimulatory effect, wherein the oligonucleotide comprises a 3' substituted nucleoside at a position adjacent to, and on the 5' and/or 3' side of the CpG dinucleotide. In preferred embodiments, CpG-containing oligonucleotides used in this aspect of the invention include a 2'–5' linkage between the 2' position of a 3' substituted nucleoside and the 5' position of another nucleoside, which may or may not be a 3' substituted nucleoside.

In the methods according to this aspect of the invention, preferably, administration of oligonucleotides should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

The method according to this aspect of the invention is useful in animal models of disease or gene expression, and is further useful for the therapeutic treatment of human or animal disease.

In a fourth aspect, the invention provides a method for reducing the immunostimulatory effect of a CpG-containing oligonucleotide. The method according to this aspect of the invention comprises introducing an uncharged internucleoside linkage into the oligonucleotide at a position adjacent to, and on the 5' side of the CpG dinucleotide.

For purposes of the fourth, fifth and sixth aspects of the invention, preferred uncharged internucleoside linkages include, without limitation, phosphoramidate linkages, carbamate linkages, peptide linkages, alkylphosphonate linkages, particularly methylphosphonate linkages, and further include linkages in which the non-bridging oxygen atom of the phosphate is either covalently bonded to or substituted by a chemical moiety selected from halogen (preferably Cl, Br, or F), lower alkyl group containing 1–6 saturated or unsaturated carbon atoms, aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; and, an amino group.

The method according to this aspect of the invention can be conveniently carried out using any of the well-known synthesis techniques by simply using the appropriate P-substituted monomer synthon in the synthesis process in the cycle immediately following the incorporation of the CpG dinucleotide. Preferred monomers include phosphites, phosphotriesters and H-phosphites. Thus, for purposes of the invention, "introducing an uncharged internucleoside linkage into the oligonucleotide at a position adjacent to, and on the 5' side of the CpG dinucleotide" simply means synthesizing an oligonucleotide that has an uncharged internucleoside nucleoside linkage at such a position, i.e., the 5' position of the C of the CpG forms part of the uncharged linkage.

Synthesis of oligonucleotides containing uncharged internucleoside linkages is well known in the art.

In a fifth aspect, the invention provides a CpG-containing oligonucleotide having a reduced immunostimulatory effect, wherein the oligonucleotide comprises an uncharged internucleoside linkage at a position adjacent to, and on the 5' side of the CpG dinucleotide. Preferably, such oligonucleotides will have from about 12 to about 50 nucleotides, most preferably from about 12 to about 35 nucleotides. Preferred oligonucleotides according to this aspect of the invention are complementary to a gene or gene transcript. More preferably, such oligonucleotides have antisense activity. In some preferred embodiments, the oligonucleotide has only one uncharged internucleoside linkage for each CpG dinucleotide present in the oligonucleotide. In some preferred embodiments, the oligonucleotide has only one an uncharged internucleoside linkage.

In a sixth aspect, the invention provides a method for obtaining an antisense-specific reduction in the expression of a gene in a mammal, the method comprising administering to the mammal a CpG-containing oligonucleotide having a reduced immunostimulatory effect, wherein the oligonucleotide comprises an uncharged internucleoside linkage at a position adjacent to, and on the 5' side of the CpG dinucleotide.

In the methods according to this aspect of the invention, preferably, administration of oligonucleotides should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

The method according to this aspect of the invention is useful in animal models of disease or gene expression, and is further useful for the therapeutic treatment of human or animal disease.

In a seventh aspect, the invention provides a method for reducing the immunostimulatory effect of a CpG-containing oligonucleotide. The method according to this aspect of the invention comprises introducing a 2'–5' internucleoside linkage into the oligonucleotide at a position adjacent to, and on the 5' side of the CpG dinucleotide.

The method according to this aspect of the invention can be conveniently carried out using any of the well-known synthesis techniques by simply using the appropriate 3'-protected monomer synthon in the synthesis process in the cycle immediately following the incorporation of the CpG dinucleotide. Preferred monomers include phosphoramidites, phosphotriesters and H-phosphonates.

Thus, for purposes of the invention, "introducing a 2'–5' internucleoside linkage into the oligonucleotide at a position adjacent to, and on the 5' side of the CpG dinucleotide" simply means synthesizing an oligonucleotide that has an uncharged internucleoside nucleoside linkage at such a position, i.e., the 5' position of the C of the CpG forms part of the 2'–5' linkage. Synthesis of oligonucleotides containing 2'–5' internucleoside linkages is well known in the art.

In an eighth aspect, the invention provides a CpG-containing oligonucleotide having a reduced immunostimulatory effect, wherein the oligonucleotide comprises a 2'–5' internucleoside linkage at a position adjacent to, and on the 5' side of the CpG dinucleotide. Preferably, such oligonucleotides will have from about 12 to about 50 nucleotides, most preferably from about 12 to about 35 nucleotides. Preferred oligonucleotides according to this aspect of the invention are complementary to a gene or gene transcript. More preferably, such oligonucleotides have antisense activity. In some preferred embodiments, the oligonucleotide has only one 2'–5' internucleoside linkage for each CpG dinucleotide present in the oligonucleotide. In some preferred embodiments, the oligonucleotide has only one an 2'–5' internucleoside linkage.

In a ninth aspect, the invention provides a method for obtaining an antisense-specific reduction in the expression of a gene in a mammal, the method comprising administering to the mammal a CpG-containing oligonucleotide having a reduced immunostimulatory effect, wherein the oligonucleotide comprises a 2'–5' internucleotide linkage at a position adjacent to, and on the 5' side of the CpG dinucleotide.

In the methods according to this aspect of the invention, preferably, administration of oligonucleotides should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

The method according to this aspect of the invention is useful in animal models of disease or gene expression, and is further useful for the therapeutic treatment of human or animal disease.

In a tenth aspect, the invention provides a method for increasing the immunostimulatory effect of a CpG-containing oligonucleotide. The method according to this aspect of the invention comprises introducing into the oligonucleotide a 3' substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide. In preferred embodiments, this method includes creating a 2'–5' linkage between the 2' position of a 3' substituted nucleoside and the 5' position of another nucleoside, which may or may not be a 3' substituted nucleoside.

For purposes of the tenth aspect of the invention, an "antisense oligonucleotide" is an oligonucleotide that is exactly complementary to a gene or gene transcript, and capable of reducing the expression of the gene or gene transcript to which it is exactly complementary.

The method according to this aspect of the invention can be conveniently carried out using any of the well-known synthesis techniques by simply using the appropriate 3' substituted monomer synthon in the synthesis process in the cycle immediately following the incorporation of the CpG dinucleotide. Preferred monomers include phosphoramidites, phosphotriesters and H-phosphonates. Thus, for purposes of the invention, "introducing into the oligonucleotide a 3' substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof." simply means synthesizing an oligonucleotide that has a 3' substituted nucleoside at such a position or positions.

In a eleventh aspect, the invention provides CpG-containing oligonucleotides having increased immunostimulatory effects, the oligonucleotide comprising a 3' substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain embodiments, the oligonucleotide is not an antisense oligonucleotide. In preferred embodiments, CpG-containing oligonucleotides according to this aspect of the invention include a 2'–5' linkage between the 2' position of a 3' substituted nucleoside and the 5' position of another nucleoside, which may or may not be a 3' substituted nucleoside.

Preferred oligonucleotides according to the fourteenth aspect of the invention are from about 6 to about 50 nucleotides in length, and may further comprise modified internucleotide linkages or modified sugars to improve stability, bioavailability, or other clinically relevant features.

In a twelfth aspect, the invention provides a method for inducing an immune response in a mammal, the method comprising administering to the mammal an oligonucleotide comprising a 3'-substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide. In preferred embodiments, CpG-containing oligonucleotides used in this aspect of the invention include a 2'–5' linkage between the 2' position of a 3' substituted nucleoside and the 5' position of another nucleoside, which may or may not be a 3' substituted nucleoside.

In the methods according to this aspect of the invention, preferably, administration of oligonucleotides should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

In certain preferred embodiments, oligonucleotides according to the invention are administered in combination with vaccines and/or adjuvants to enhance the specificity or magnitude of the immune response. Either the oligonucleotide or the vaccine, or both may optionally be linked to an immunogenic protein, such as keyhole limpet hemocyanin, cholera toxin B subunit, or any other immunogenic carrier protein. Any of the plethora of adjuvants may be used, including, without limitation, Freund's complete adjuvant. For purposes of this aspect "in combination with" means in the course of treating the same disease in the same patient, and includes administering the oligonucleotide and/or the vaccine and/or the adjuvant in any order, including simultaneous administration, as well as temporally spaced order of up to several days apart. Such combination treatment may also include more than a single administration of the oligonucleotide, and/or independently the vaccine, and/or independently the adjuvant. The administration of the oligonucleotide and/or vaccine and/or adjuvant may be by the same or different routes.

The method according to this aspect of the invention is useful for model studies of the immune system, and is further useful for the therapeutic treatment of human or animal disease.

In a thirteenth aspect, the invention provides a method for increasing the immunostimulatory effect of a CpG-containing oligonucleotide. The method according to this aspect of the invention comprises introducing into the oligonucleotide an uncharged internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. In certain preferred embodiments, the oligonucleotide is not an antisense oligonucleotide.

For purposes of the thirteenth, fourteenth and fifteenth aspects of the invention, preferred uncharged internucleoside linkages include, without limitation, phosphoramidate linkages, carbamate linkages, peptide linkages, alkylphosphonate linkages, particularly methylphosphonate linkages, and further include linkages in which the non-bridging oxygen atom of the phosphate is either covalently bonded to or substituted by a chemical moiety selected from halogen (preferably Cl, Br, or F), lower alkyl group containing 1–6 saturated or unsaturated carbon atoms, aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; and, an amino group.

The method according to this aspect of the invention can be conveniently carried out using any of the well-known synthesis techniques by simply using the appropriate P-substituted monomer synthon in the synthesis process in the cycle immediately following the incorporation of the CpG dinucleotide. Preferred monomers include phosphites, phosphotriesters and H-phosphites. Thus, for purposes of the invention, "introducing into the oligonucleotide an uncharged internucleoside linkage at a position" simply means synthesizing an oligonucleotide that has an uncharged internucleoside nucleoside linkage at such a position, i.e., counting from the C of the CpG, the uncharged internucleoside linkage is the 3' linkage of that nucleoside. Synthesis of oligonucleotides containing uncharged internucleoside linkages is well known in the art.

In a fourteenth aspect, the invention provides CpG-containing oligonucleotides having increased immunostimulatory effects, the oligonucleotide comprising an uncharged internucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, 7th nucleoside 3' to the CpG dinucleotide, 8th nucleoside 3' to the CpG dinucleotide, 9th nucleoside 3' to the CpG dinucleotide, 10th nucleoside 3' to the CpG dinucleotide, and combinations thereof. Preferred oligonucleotides according to this aspect of the invention are complementary to a gene or gene transcript. More preferably, such oligonucleotides have antisense activity. In some preferred embodiments, the oligonucleotide has only one uncharged internucleoside linkage for each CpG dinucleotide present in the oligonucleotide. In some preferred embodiments, the oligonucleotide has only one an uncharged internucleoside linkage.

Preferred oligonucleotides according to the fourteenth aspect of the invention are from about 6 to about 50 nucleotides in length, and may further comprise modified internucleotide linkages or modified sugars to improve stability, bioavailability, or other clinically relevant features.

In a fifteenth aspect, the invention provides a method for inducing an immune response in a mammal, the method comprising administering to the mammal an oligonucleotide comprising an uncharged internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, $5^{th}$ nucleoside 3' to the CpG dinucleotide, $6^{th}$ nucleoside 3' to the CpG dinucleotide, $7^{th}$ nucleoside 3' to the CpG dinucleotide, $8^{th}$ nucleoside 3' to the CpG dinucleotide, $9^{th}$ nucleoside 3' to the CpG dinucleotide, $10^{th}$ nucleoside 3' to the CpG dinucleotide, and combinations thereof. In certain preferred embodiments, the oligonucleotide is not an antisense oligonucleotide.

In the methods according to this aspect of the invention, preferably, administration of oligonucleotides should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

In certain preferred embodiments, oligonucleotides according to the invention are administered in combination with vaccines and/or adjuvants to enhance the specificity or magnitude of the immune response. Either the oligonucleotide or the vaccine, or both may optionally be linked to an immunogenic protein, such as keyhole limpet hemocyanin, cholera toxin B subunit, or any other immunogenic carrier protein. Any of the plethora of adjuvants may be used, including, without limitation, Freund's complete adjuvant. For purposes of this aspect "in combination with" means in the course of treating the same disease in the same patient, and includes administering the oligonucleotide and/or the vaccine and/or the adjuvant in any order, including simultaneous administration, as well as temporally spaced order of up to several days apart. Such combination treatment may also include more than a single administration of the oligonucleotide, and/or independently the vaccine, and/or independently the adjuvant. The administration of the oligonucleotide and/or vaccine and/or adjuvant may be by the same or different routes.

In a sixteenth aspect, the invention provides a method for increasing the immunostimulatory effect of a CpG-containing oligonucleotide. The method according to this aspect of the invention comprises introducing into the oligonucleotide a 2'–5' internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, $5^{th}$ nucleoside 3' to the CpG dinucleotide, $6^{th}$ nucleoside 3' to the CpG dinucleotide, $7^{th}$ nucleoside 3' to the CpG dinucleotide, $8^{th}$ nucleoside 3' to the CPG dinucleotide, $9^{th}$ nucleoside 3' to the CpG dinucleotide, $10^{th}$ nucleoside 3' to the CpG dinucleotide, and combinations thereof. In certain preferred embodiments, the oligonucleotide is not an antisense oligonucleotide.

The method according to this aspect of the invention can be conveniently carried out using any of the well-known synthesis techniques by simply using the appropriate 3'-protected monomer synthon in the synthesis process in the cycle immediately following the incorporation of the CpG dinucleotide. Preferred monomers include phosphoramidites, phosphotriesters and H-phosphonates. Thus, for purposes of the invention, "introducing into the oligonucleotide a 2'–5' internucleoside linkage at a position" simply means synthesizing an oligonucleotide that has a 2'–5' internucleoside nucleoside linkage at such a position, i.e., counting from the C of the CpG, the uncharged internucleoside linkage is the 3' linkage of that nucleoside. Synthesis of oligonucleotides containing 2'–5' internucleoside linkages is well known in the art.

In a seventeenth aspect, the invention provides CpG-containing oligonucleotides having increased immunostimulatory effects, the oligonucleotide comprising a 2'–5' internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, $5^{th}$ nucleoside 3' to the CpG dinucleotide, $6^{th}$ nucleoside 3' to the CpG dinucleotide, $7^{th}$ nucleoside 3' to the CpG dinucleotide, $8^{th}$ nucleoside 3' to the CpG dinucleotide, $9^{th}$ nucleoside 3' to the CpG dinucleotide, $10^{th}$ nucleoside 3' to the CpG dinucleotide, and combinations thereof.

Preferred oligonucleotides according to the seventeenth aspect of the invention are from about 6 to about 50 nucleotides in length, and may further comprise modified internucleotide linkages or modified sugars to improve stability, bioavailability, or other clinically relevant features.

In an eighteenth aspect, the invention provides a method for inducing an immune response in a mammal, the method comprising administering to the mammal an oligonucleotide comprising a 2'–5' internucleoside linkage at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, $5^{th}$ nucleoside 3' to the CpG dinucleotide, $6^{th}$ nucleoside 3' to the CpG dinucleotide, $7^{th}$ nucleoside 3' to the CpG dinucleotide, if $8^{th}$ nucleoside 3' to the CpG dinucleotide, $9^{th}$ nucleoside 3' to the CpG dinucleotide, $10^{th}$ nucleoside 3' to the CpG dinucleotide, and combinations thereof. In certain preferred embodiments, the oligonucleotide is not an antisense oligonucleotide.

In the methods according to this aspect of the invention, preferably, administration of oligonucleotides should be parenteral, oral, sublingual, transdermal, topical, intranasal or intrarectal. Administration of the therapeutic compositions can be carried out using known procedures at dosages and for periods of time effective to reduce symptoms or surrogate markers of the disease. When administered systemically, the therapeutic composition is preferably administered at a sufficient dosage to attain a blood level of oligonucleotide from about 0.01 micromolar to about 10 micromolar. For localized administration, much lower concentrations than this may be effective, and much higher concentrations may be tolerated. Preferably, a total dosage of oligonucleotide will range from about 0.1 mg oligonucleotide per patient per day to about 200 mg oligonucleotide per kg body weight per day. It may be desirable to administer simultaneously, or sequentially a therapeutically effective amount of one or more of the therapeutic compositions of the invention to an individual as a single treatment episode. In a preferred embodiment, after the composition of matter is administered, one or more measurement is taken of biological effects selected from the group consisting of complement activation, mitogenesis and inhibition of thrombin clot formation.

In certain preferred embodiments, oligonucleotides according to the invention are administered in combination with vaccines and/or adjuvants to enhance the specificity or magnitude of the immune response. Either the oligonucleotide or the vaccine, or both may optionally be linked to an immunogenic protein, such as keyhole limpet hemocyanin, cholera toxin B subunit, or any other immunogenic carrier protein. Any of the plethora of adjuvants may be used, including, without limitation, Freund's complete adjuvant. For purposes of this aspect "in combination with" means in the course of treating the same disease in the same patient, and includes administering the oligonucleotide and/or the vaccine and/or the adjuvant in any order, including simultaneous administration, as well as temporally spaced order of up to several days apart. Such combination treatment may also include more than a single administration of the oligonucleotide, and/or independently the vaccine, and/or independently the adjuvant. The administration of the oligonucleotide and/or vaccine and/or adjuvant may be by the same or different routes.

For purposes of all aspects of the invention, the term "oligonucleotide" includes polymers of two or more deoxyribonucleotides, or any modified nucleoside, including 2'-halo-nucleosides, 2' or 3' substituted, 2' or 3'-O-substituted ribonucleosides, deazanucleosides or any combination thereof. Such monomers may be coupled to each other by any of the numerous known internucleoside linkages. In certain preferred embodiments, these internucleoside linkages may be phosphodiester, phosphotriester, phosphorothioate, or phosphoramidate linkages, 2'–5' linkages of any of the forgoing, or combinations thereof. The term oligonucleotide also encompasses such polymers having chemically modified bases or sugars and/or having additional substituents, including without limitation lipophilic groups, intercalating agents, diamines and adamantane. The term oligonucleotide also encompasses PNA, LNA and oligonucleotides comprising non-pentose sugar (e.g. hexose) backbones or backbone sections. For purposes of the invention the term "3'-O-substituted" means substitution of the 3' position of the pentose moiety with a halogen (preferably Cl, Br, or F), or an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 3' substitution may be with a hydroxy group (to produce a ribonucleoside), an amino or a halo group. For purposes of all aspects of the invention, the terms "CpG" or "CpG dinucleotide" means the dinucleotide 5'-cytidine-guanidine-3', wherein p is an internucleotide linkage, and wherein the sugar backbone of the dinucleotide may be ribose, deoxyribose, or 3' substituted ribose, or combinations thereof. In preferred embodiments of the first three aspects of the invention, p is selected from phosphodiester, phosphorothioate, alkylphosphonate, phosphotriester, stereospecific (Rp or Sp) phosphorothioate or alkylphosphonate, and 2'–5' covalent linkages of any of the above. The non-phosphodiester, non-phosphorothioate embodiments will further reduce immunostimulatory effects. In preferred embodiments of the last three aspects of the invention, p is selected from phosphodiester, phosphorothioate and phosphordithioate.

The following examples are intended to further illustrate certain preferred embodiments of the invention, and are not intended to limit the scope of the invention.

EXAMPLE 1

Preparation of Oligonucleotides Containing Site-specific 3'-O-methylribonucleosides Oligonucleotides were synthesized using solid phase (1 μmole scale) posphoramidite chemistry on an automated DNA synthesizer (Expedite 8909, PE Biosystems, MA). The segment of 3'-O-methylribonucleoside phosphorothioate was incorporated into the oligonucleotide using 3'-O-methyl-2'-cyanoethyl ribonucleoside phosphoramidites (ChemGenes, MA). Oligonucleotide was sulfurized using 3H-1,2-benzodithiole-3-one-1,1-dioxide. Oligonucleotides were purified by preparative reversed-phase HPLC and characterized by CGE (data process through PE Nelson Turbochrom software) and MALDI-TOF mass analysis (Bruker Profelx III mass spectrometer).

EXAMPLE 2

Modulation of Immulostimulatory Effect in vitro: 3' Substitutions

To evaluate the immunostimulatory activity of oligonucleotides in the present study, a mouse spleen cell proliferation assay in which mouse spleen cells were cultured with oligonucleotide at concentrations of 0.1, 1.0 and 10 μg/ml.

The oligos shown in Table 1 were used for these studies.

TABLE 1

| Oligo No. | Sequence and Modification |
|---|---|
| 1 | T C C A T G A C G T T C C T G A T G C |
| 2 | T C C A T G A C G T T C C T G A T G C |
| 3 | T C C A U G A C G T T C C T G A T G C |
| 4 | T C C A T G A C G T T C C T G A T G C |
| 5 | T C C A T G A C G U T C C T G A T G C |

Bold lettering indicates 3'-O-methyl modification

We used a PS-oligonucleotide containing a single CpG dinucleotide (Oligo 1) and Oligos 2–5 in which substitution of one deoxynucleoside was carried out with modified nucleosides at specific sites. Results are presented in FIG. 1.

Substitution with 3'-O-methyl ribonucleosides in Oligos 2.5 simultaneously led to incorporation of 2'–5' internucleoside linkages. Substitution 5' of the CpG dinucleotide with no intervening nucleosides (Oligo 2) diminished immunostimulatory activity. Surprisingly, substitution 3' of the CpG dinucleotide with no intervening nucleosides (Oligo 5) also diminished immunostimulatory activity. In addition, Oligos 3 and 4, with 3'-O-methylribonucleoside substitution 5' to the CpG dinucleotide increase immunostimulatory activity (indices of 4.6+/−0.43 and 5.7+/−0.87, respectively.

EXAMPLE 3

Modulation of Immulostimulatory Effect in vivo: Methylphosphonate Substitutions To test the applicability of the in vitro results to an in vivo model, selected oligonucleotides were administered to mice and the degree of splenomegaly was measured as an indicator of the level of immunostimulatory activity. A single dose of 5 mg/kg was administered to Balb/c mice (female, 4–6 weeks old, Harlan Spraque Dawley Inc) intraperitonealy. The mice were sacrificed 72 hours after administration and spleens were harvested and weighed. Positive control Oligo 1 caused A 74% increase in spleen weight compared to negative control mice receiving only PBS.

Figure 2:
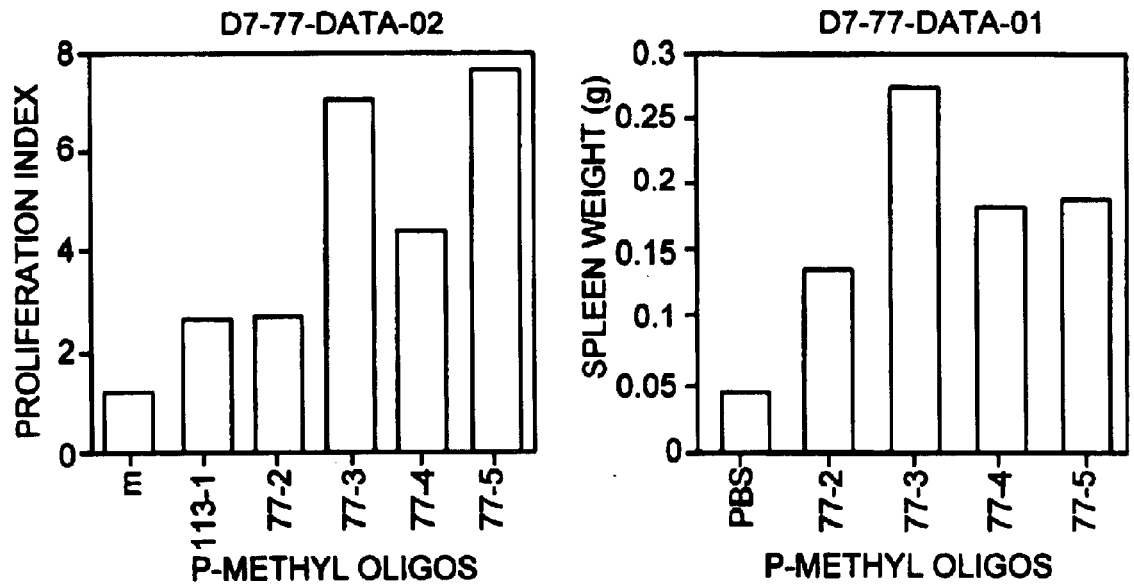
FIG. 2 (SEQ ID NOS 1, 6, 4, 7 and 8, respectively, in order of appearance) shows results of a proliferation assay of mouse spleen cells and shows spleen enlargement in mice administered no oligonucleotide (c), or various unsubstituted or methylphosphonate substituted oligonucleotides. Underlined nucleosides have a methylphosphonate linkage at the 3' position.

Oligonucleotides containing methylphosphonate internucleotide linkages are shown in FIG. 2. Oligonucleotides were prepared having methylphosphonate linkages 3 or 4 nucleotides 5' to the CpG dinucleotide, or 2 or 3 nucleotides 3' to the CpG dinucleotide. As shown in FIG. 2, all of these oligonucleotides were more immunostimulatory than Oligo 1 in both the mouse spleen cell proliferation assay and the spleen enlargement assay.

What is claimed is:

1. A method for increasing the immunostimulatory effect of a CpG-containing oligonucleotide, the method comprising introducing into the oligonucleotide a 3'-pentose substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, and combinations thereof.

2. The method according to claim 1, wherein the oligonucleotide is not an antisense oligonucleotide.

3. A CpG-containing oligonucleotide having increased immunostimulatory effects, the oligonucleotide comprising a 3'-pentose substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CPG dinucleotide, and combinations thereof.

4. The oligonucleotide according to claim 3, wherein the oligonucleotide is not an antisense oligonucleotide.

5. The oligonucleotide according to claim 3, wherein the oligonucleotide is from about 6 to about 50 nucleotides in length.

6. The oligonucleotide according to claim 3, wherein the oligonucleotide further comprises modified internucleotide linkages or modified sugars to improve stability.

7. A method for enhancing an immune response in a mammal, the method comprising administering to the mammal an oligonucleotide comprising a 3'-pentose substituted nucleoside at a position selected from the group consisting of 3rd nucleoside 5' to the CpG dinucleotide, 4th nucleoside 5' to the CpG dinucleotide, 5th nucleoside 5' to the CpG dinucleotide, 6th nucleoside 5' to the CpG dinucleotide, 2nd nucleoside 3' to the CpG dinucleotide, 3rd nucleoside 3' to the CpG dinucleotide, 4th nucleoside 3' to the CpG dinucleotide, 5th nucleoside 3' to the CpG dinucleotide, 6th nucleoside 3' to the CpG dinucleotide, and combinations thereof.

8. The method according to claim 7, wherein the oligonucleotide is not an antisense oligonucleotide.

* * * * *